(12) United States Patent
Kruszynski (10) Patent No.: US 7,568,605 B2
(45) Date of Patent: Aug. 4, 2009

(54) SURGICAL STAPLER SHAFT COVER

(75) Inventor: Michael L. Kruszynski, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 135 days.

(21) Appl. No.: 11/386,088

(22) Filed: Mar. 22, 2006

(65) Prior Publication Data

US 2007/0221702 A1    Sep. 27, 2007

(51) Int. Cl.
*A61B 17/10* (2006.01)
(52) U.S. Cl. .................. 227/179.1; 227/175.1; 227/19
(58) Field of Classification Search .............. 227/19, 227/175.1, 179.1
See application file for complete search history.

(56) References Cited

U.S. PATENT DOCUMENTS

| | | | | |
|---|---|---|---|---|
| 3,692,224 A | * | 9/1972 | Astafiev et al. | 227/19 |
| 4,728,020 A | * | 3/1988 | Green et al. | 227/19 |
| 4,869,414 A | * | 9/1989 | Green et al. | 227/19 |
| 4,930,674 A | | 6/1990 | Barak | |
| 5,104,025 A | * | 4/1992 | Main et al. | 227/175.1 |
| 5,251,801 A | | 10/1993 | Ruckdeschel et al. | |
| 5,355,897 A | * | 10/1994 | Pietrafitta et al. | 128/898 |
| 5,395,030 A | * | 3/1995 | Kuramoto et al. | 227/179.1 |
| 6,805,273 B2 | * | 10/2004 | Bilotti et al. | 227/180.1 |
| 2004/0199182 A1 | | 10/2004 | Milliman et al. | |
| 2005/0143756 A1 | | 6/2005 | Jankowski | |
| 2005/0236459 A1 | | 10/2005 | Gresham | |

FOREIGN PATENT DOCUMENTS

EP    1790295    5/2007

\* cited by examiner

*Primary Examiner*—Brian D Nash
(74) *Attorney, Agent, or Firm*—Welsh & Flaxman LLC (57) ABSTRACT

A cover for a surgical stapler includes a cover body shaped and dimensioned for fitting about a shaft of a surgical stapler, the cover body having a substantially smooth outer surface and a recessed section shaped and dimensioned for positioning about a surgical stapler.

10 Claims, 9 Drawing Sheets

SURGICAL STAPLER SHAFT COVER

BACKGROUND OF THE INVENTION

1. Field of the Invention

The present invention relates to a surgical stapling and cutting instrument. More particularly, the present invention relates to a surgical stapling and cutting instrument having a shaft cover permitting use for hand assisted laparoscopic surgery.

2. Description of the Prior Art

Surgical stapling and cutting instruments (for example, linear surgical staplers) are commonly utilized in the diagnosis and treatment of pathologies treated by staple resection. Surgical stapling and cutting instruments provide a mechanism to extend the transluminal exploitation of mechanical suturing devices introduced via the anal canal, mouth, stomach and service accesses.

These instruments generally include a support frame, an anvil attached to the support frame and a cartridge module carrying a plurality of staples. The instruments also include a driver within the cartridge module which pushes all of the staples out simultaneously into the anvil to form the staples into a generally B-shape, suturing tissue together. In addition, these instruments include approximation mechanisms for moving the cartridge module from a spaced position relative to the anvil for accepting tissue therebetween to a closed position where the tissue is clamped between the anvil and the cartridge module. The instruments also commonly include a cutting blade for cutting the tissue in conjunction with the stapling thereof. Finally, the instruments include a firing mechanism for moving the staple driver forward to form the staples against the anvil.

These surgical stapling and cutting instruments are known to be utilized in conjunction with hand assisted laparoscopic surgery. However, when they are currently utilized in hand assisted laparoscopic surgery, conventional surgical stapling and cutting instruments are employed. As those skilled in the art will certainly appreciate, conventional surgical stapling and cutting instruments include sharp edges which may catch and/or tear the membrane of the seals through which they are passed during hand assisted laparoscopic surgery. In addition, surgical stapling and cutting instruments include a variety of unprotected moving parts which may become adversely affected by the bodily tissues and fluids they encounter during hand assisted laparoscopic surgery.

With this in mind, it is desirable to further adapt the surgical stapling and cutting instruments to optimize their usage in the performance of hand assisted laparoscopic surgery. The present invention provides a cover designed to optimize the performance of a surgical stapling and cutting instrument used during hand assisted laparoscopic surgery.

SUMMARY OF THE INVENTION

It is, therefore, an object of the present invention to provide a cover for the shaft of a surgical stapler. The cover includes a cover body shaped and dimensioned for fitting about a shaft of a surgical stapler, the cover body including a substantially smooth outer surface and a recessed section shaped and dimensioned for positioning about a surgical stapler.

It is also an object of the present invention to provide a cover wherein the cover body includes a first cover member and a second cover member.

It is another object of the present invention to provide a cover wherein the first cover member and the second cover member are connected by a living hinge.

It is a further object of the present invention to provide a cover wherein the first cover member and second cover member are selectively connected via a snap connection.

It is also an object of the present invention to provide a cover wherein the first cover member includes an outer surface and an opposed inner surface including a central recess and the second cover member includes an outer surface and an opposed inner surface including a central recess.

It is still another object of the present invention to provide a cover including at least one seal formed along the recessed section for engaging the surgical stapler.

It is also a further object of the present invention to provide a cover wherein the cover includes a first end and a second end, and a first seal is positioned adjacent the first end of the cover and a second seal is positioned adjacent the second end of the cover.

It is also an object of the present invention to provide a surgical stapler including a handle at a first proximal end and an end effector at an opposite distal end, at least one structural plate connecting the handle to the end effector. A cover is positioned about the structural plate. The cover includes a cover body shaped and dimensioned for fitting about the structural plate, the cover body including a substantially smooth outer surface and a recessed section shaped and dimensioned for positioning about the structural plate a surgical stapler.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and for teaching one skilled in the art how to make and/or use the invention.

Referring to FIGS. 1 to 5, there is shown a surgical stapling and cutting instrument, in particular, a linear surgical stapler 20, which is designed to staple and cut tissue. The linear surgical stapler 20 has a handle 21 at a first proximal end and an end effector 80 at an opposite distal end. The end effector 80 is curved in accordance with a preferred embodiment of the present invention, although the concepts underlying the present invention may be applied to a variety of surgical stapling and cutting instruments regardless of the shape of the end effector.

Figure 1:
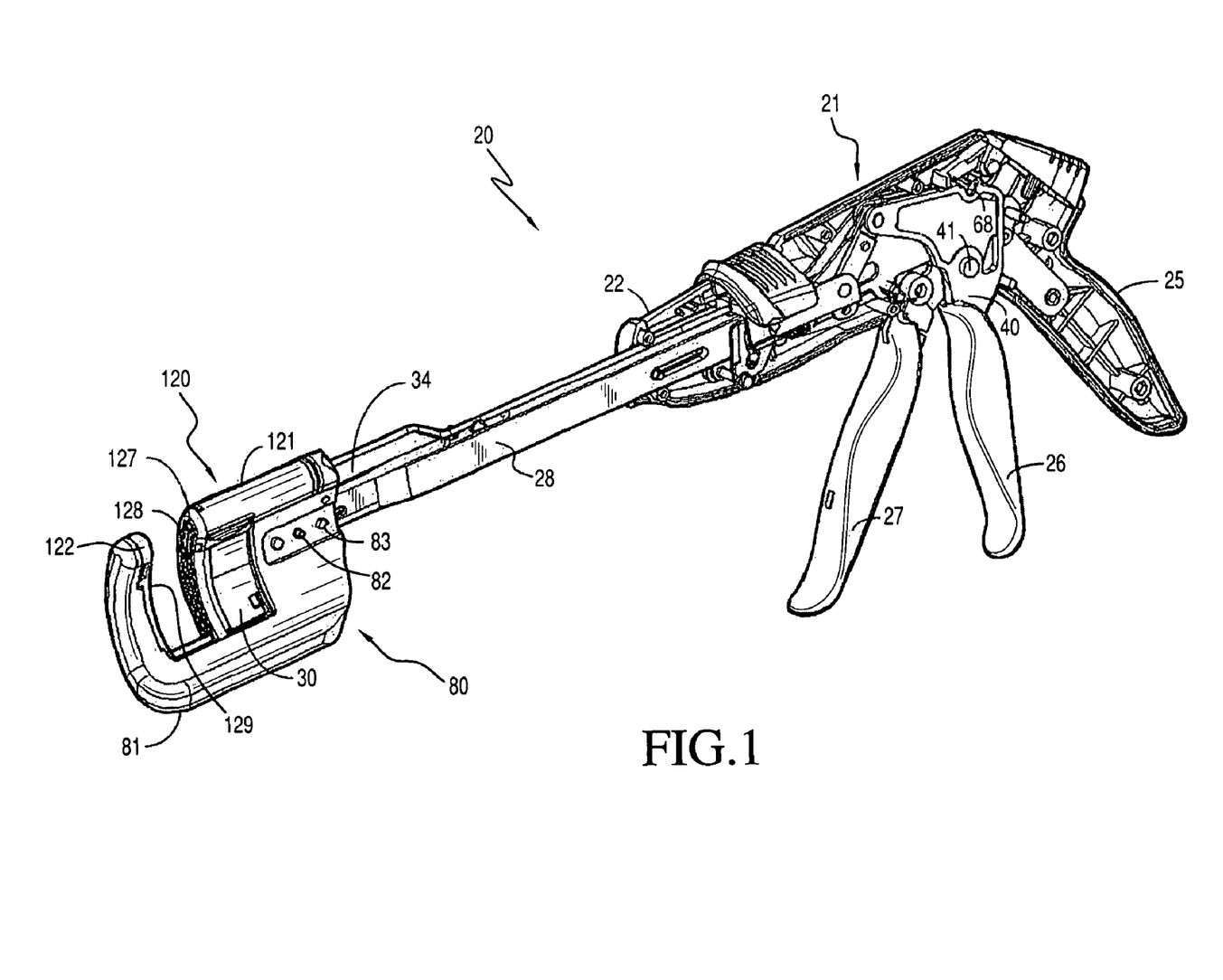
FIG. 1 is a perspective view of the linear surgical stapler in accordance with the present invention.
Figure 2:
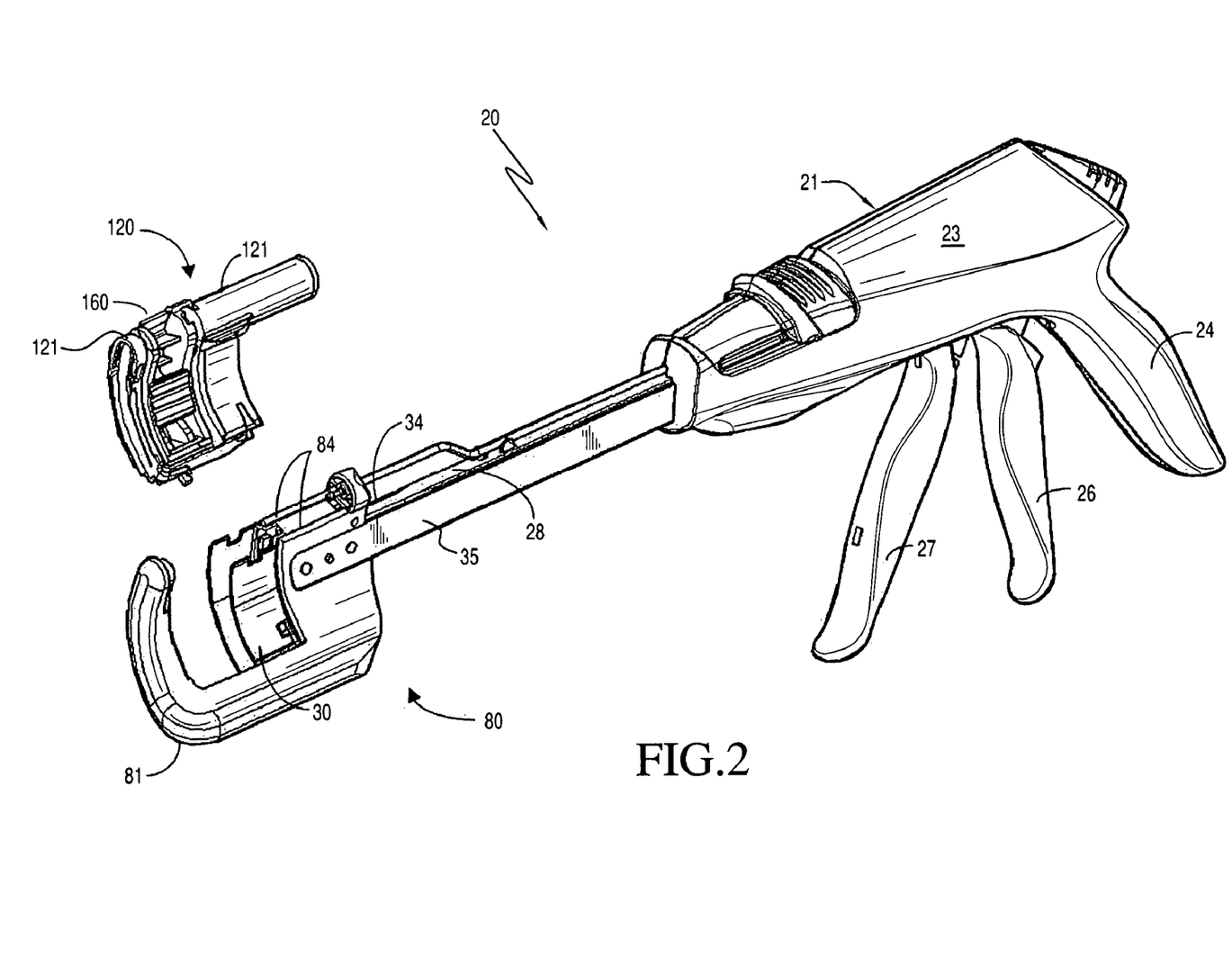
FIG. 2 is perspective view of the linear surgical stapler with the cartridge module removed.
Figure 3:
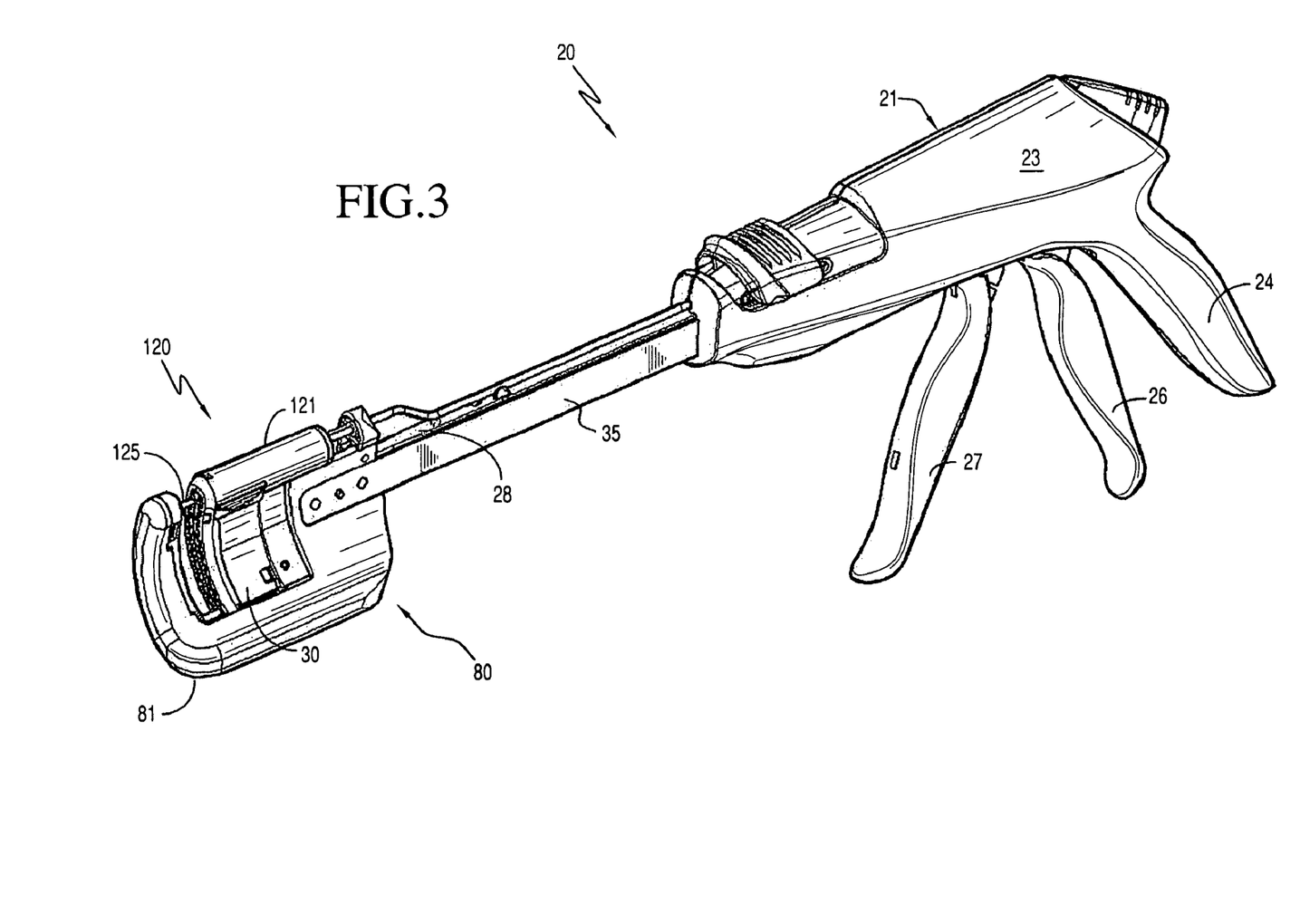
FIG. 3 is a perspective view of the linear surgical stapler with the cartridge housing moved to an intermediate position.
Figure 4:
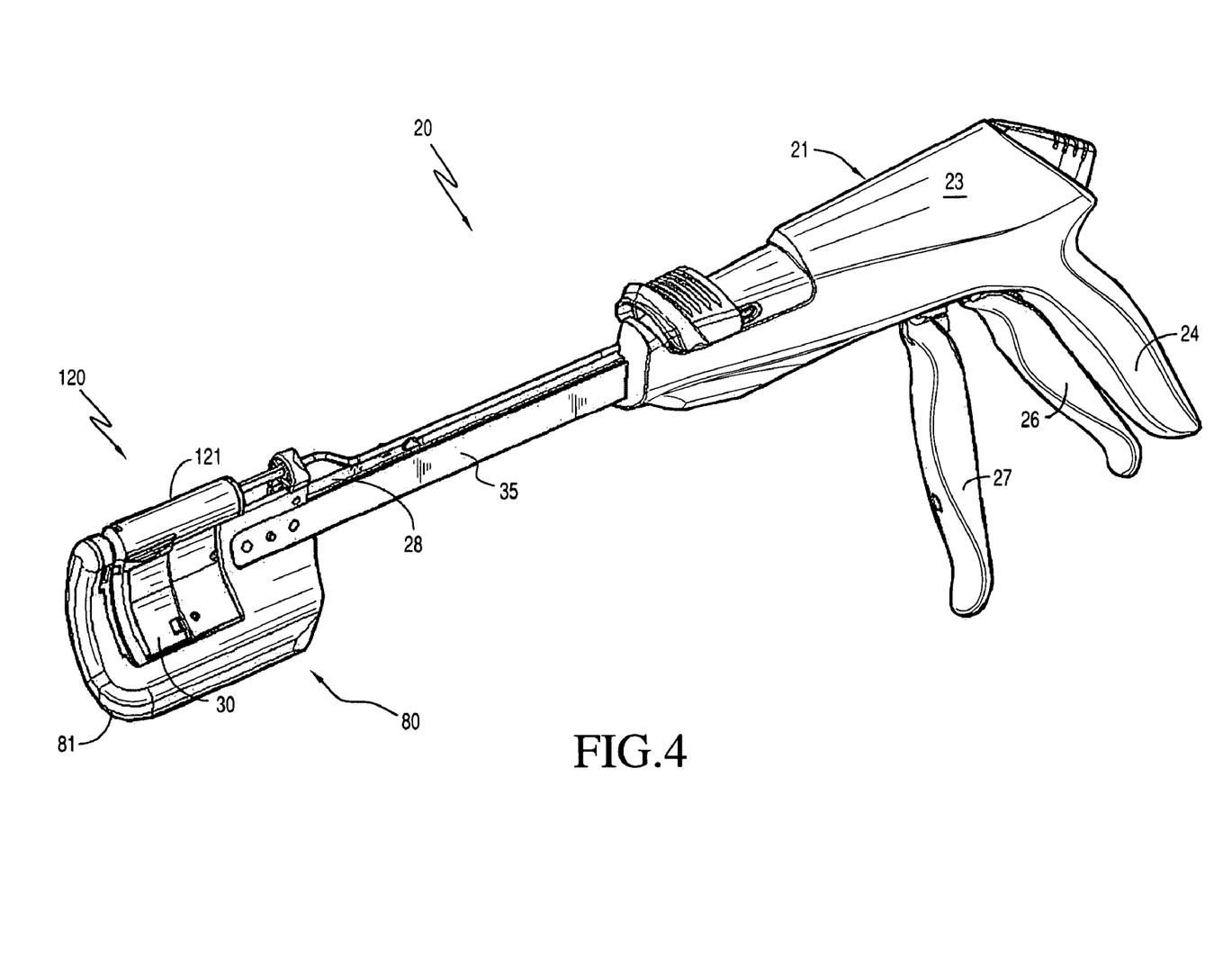
FIG. 4 is a perspective view of the linear surgical stapler with the cartridge housing moved to a closed position.
Figure 5:
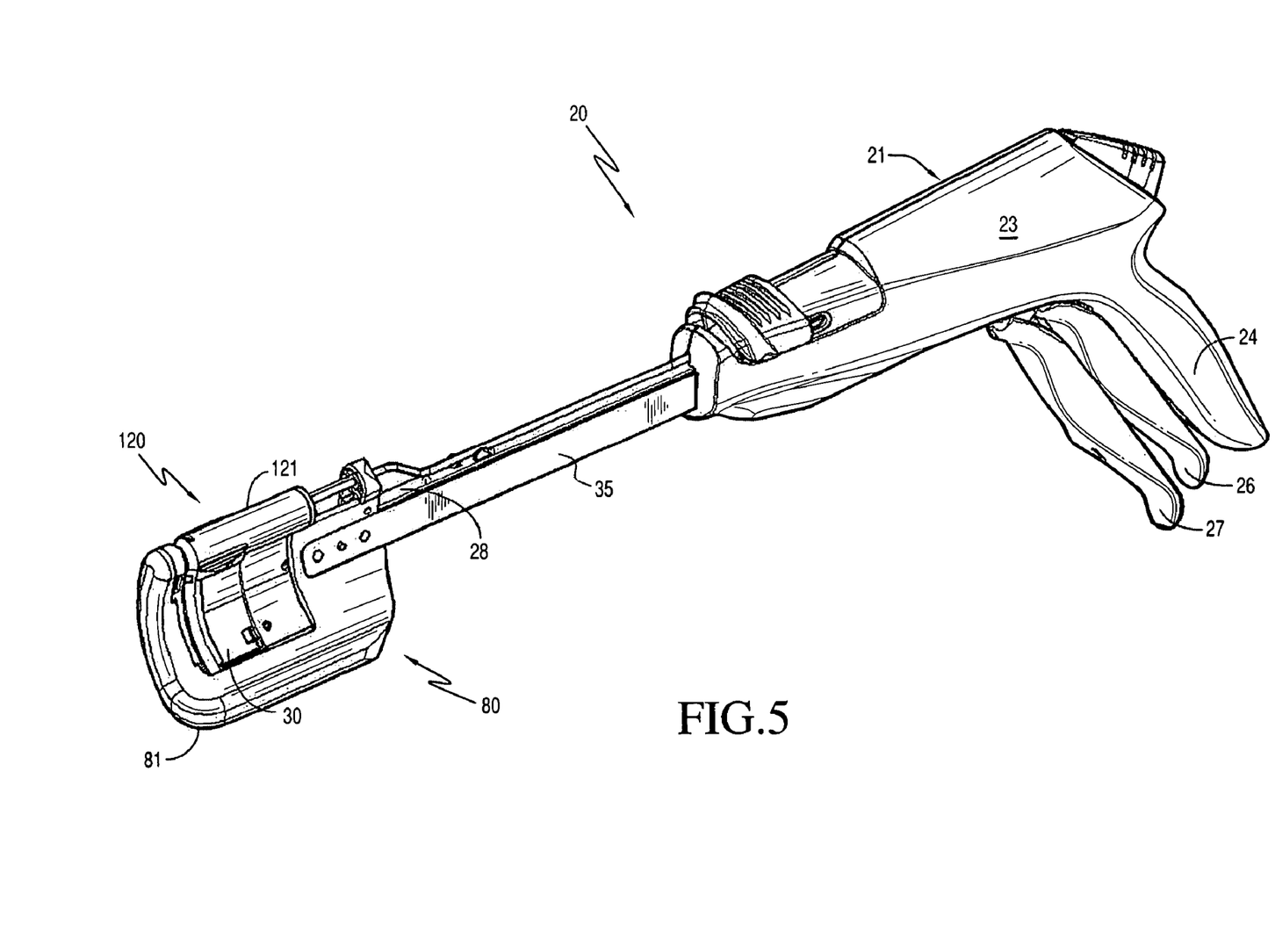
FIG. 5 is a perspective view of the linear surgical stapler with the firing trigger in a firing position.
Figure 6:
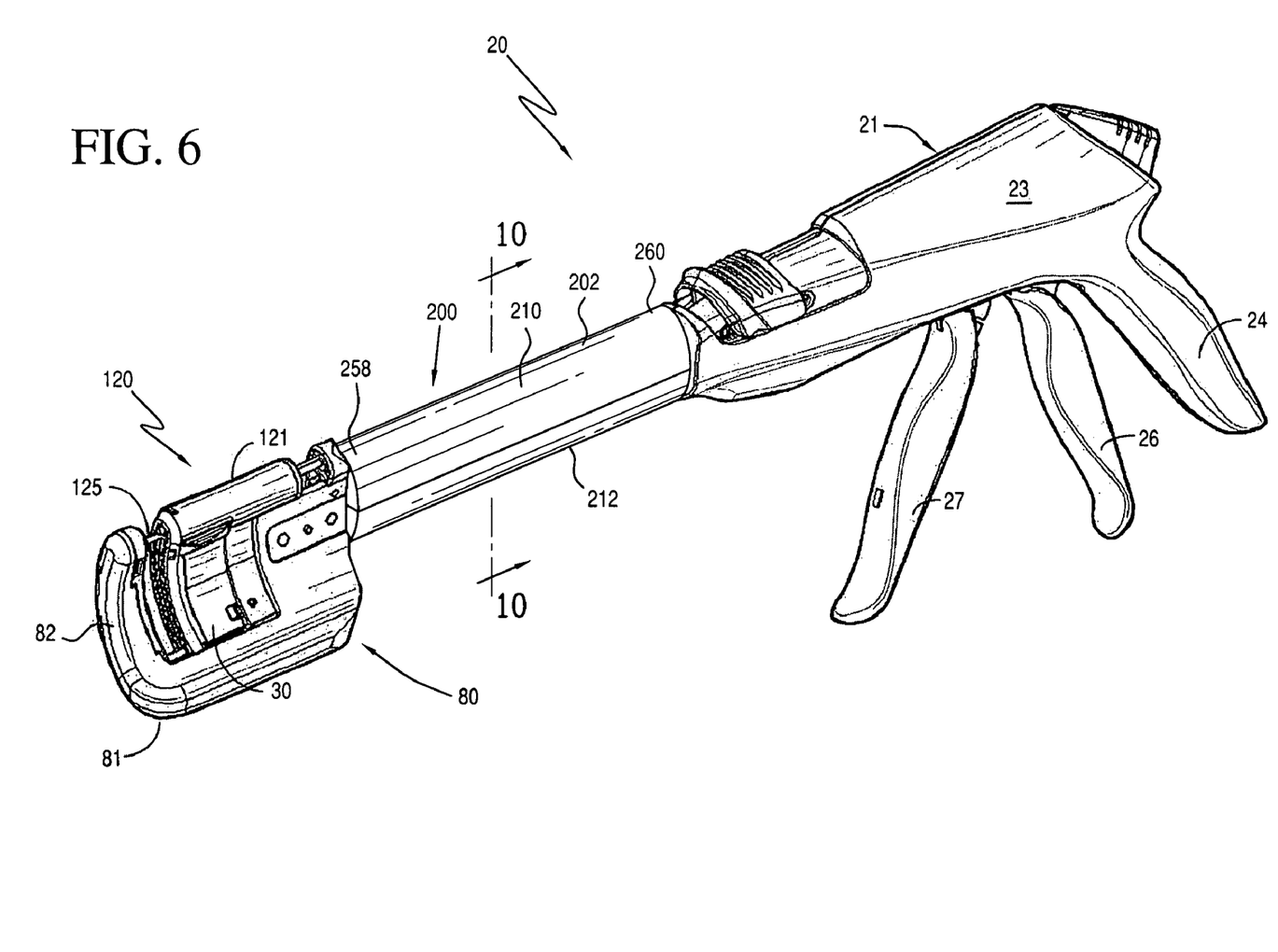
FIG. 6 is a perspective view of the linear surgical stapler with a cover in accordance with the present invention secured thereto.
Figure 7:
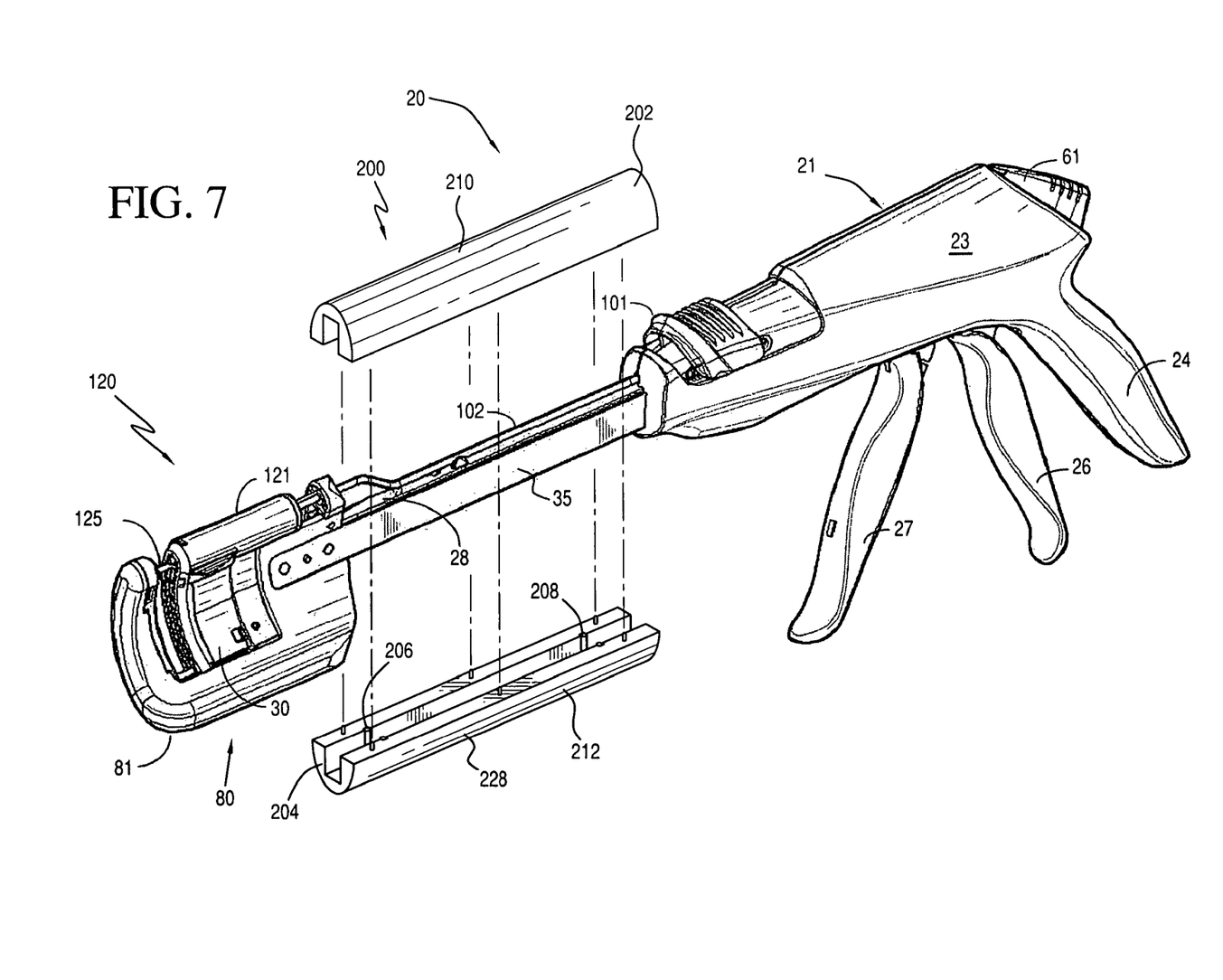
FIG. 7 is an exploded perspective view of the cover secured to the surgical stapler.
Figures 8, 9:
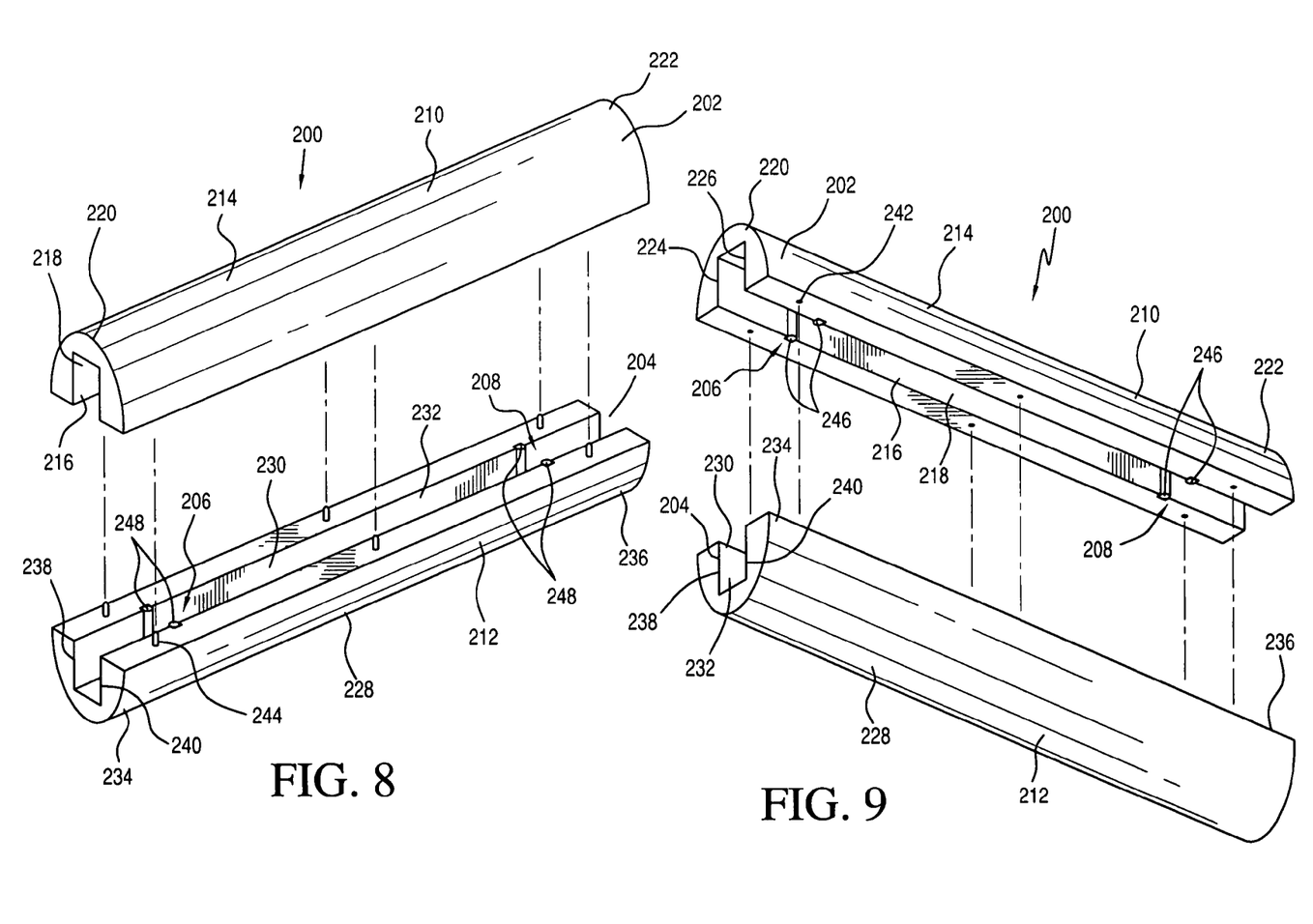
FIGS. 8 and 9 are respectively top and bottom perspective views of the cover.
Figure 10:
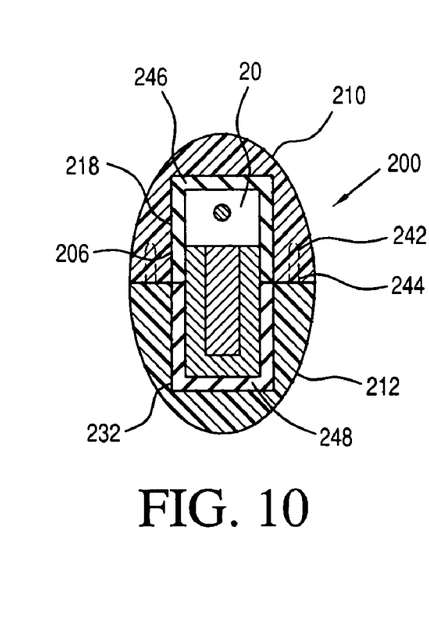
FIG. 10 is a cross sectional view of the cover on the linear surgical stapler.

Right and left hand structural plates (often called "handle plates") 34, 35, respectively, form a shaft connecting the handle 21 to the end effector 80 of the instrument (the left hand handle plate 35 is removed and not shown in FIG. 1). The handle 21 has a right hand shroud 22 coupled to a left hand shroud (the left hand shroud is not shown in FIG. 1). The handle 21 also has a body portion 23 to grip and maneuver the linear surgical stapler 20 (see FIGS. 2 to 5).

While the present end effector 80 is disclosed as being adapted for use in conjunction with a replaceable cartridge module 120 having various components, the concepts underlying the present invention could be applied to a variety of end effector and cartridge module constructions without departing from the spirit of the present invention.

The end effector 80 is a surgical fastening assembly that includes a cartridge module 120 and a C-shaped supporting structure 81. The term C-shaped is used throughout the specification to describe the concave nature of the supporting structure 81 and the cartridge module 120. The C-shaped construction facilitates enhanced functionality and the use of the term C-shaped in the present specification should be construed to include a variety of concave shapes which would similarly enhance the functionality of surgical stapling and cutting instruments. The distal end 30 of a closure member 28 is disposed to receive the cartridge module 120.

The cartridge module 120 contains a cartridge housing 121 coupled to an anvil 122. The cartridge module 120 also includes a retaining pin 125, a knife (not shown), a removable retainer 160, a tissue contacting surface 127 which displays a plurality of staple-containing slots 128 in staggered formation in one or more rows (that is, staple lines) on either side of the knife. Staples (not shown) are fired from the cartridge housing 121 against a staple-forming surface 129 of the anvil 122 that faces the tissue-contacting surface 127 of the cartridge housing 121.

As will become apparent based upon the following disclosure, the present linear surgical stapler 20 is designed as a multiple firing device with a replaceable cartridge module 120. However, it should be understood that many of the underlying concepts of the present invention may be equally applied in single firing devices without departing from the spirit of the present invention.

The supporting structure 81 of the end effector 80 is respectively attached to the right and left handle plates 34, 35, by a shoulder rivet 82 and posts 83 which extend from the supporting structure 81 into receiving holes in the handle plates 34, 35. In accordance with a preferred embodiment of the present invention, the supporting structure 81 is formed via a single piece construction. More specifically, the supporting structure 81 is formed by extrusion, for example, of aluminum, with subsequent machining to create the supporting structure 81 disclosed in accordance with the present invention. By constructing the supporting structure 81 in this manner, multiple parts are not required and the associated cost of manufacture and assembly is substantially reduced. In addition, it is believed the unitary structure of the supporting structure 81 enhances the overall stability of the present linear surgical stapler 20. In addition, the unitary extruded structure of the supporting structure 81 provides for a reduction in weight, easier sterilization since cobalt irradiation will effectively penetrate the extruded aluminum and less trauma to tissue based upon the smooth outer surface achieved via extrusion.

The handle 21 of the linear surgical stapler 20 includes a hand grip 24 which the surgeon grasps with the palm of his hand (see FIGS. 2 to 5). The hand grip 24 is composed of a right hand shroud handle 25 (see FIG. 1) and a left hand shroud handle (the left hand shroud handle is not shown in FIG. 1). Pivotally extending from the underside of the handle 21 are a closure trigger 26 and a firing trigger 27. The linear surgical stapler 20 illustrated in FIG. 1 is shown with the closure and firing triggers 26, 27 in their unactuated positions, with a cartridge module 120 inserted and with the retainer 160 removed. Consequently, the cartridge housing 121 is spaced from the anvil 122 for the placement of tissue between the cartridge housing 121 and the anvil 122.

In an effort to optimize usage of the present surgical stapler 20 in the performance of hand assisted laparoscopic surgery through a lap disc, or equivalent device, the surgical stapler 20 is provided with a cover 200 (see FIGS. 6 to 10). The cover 200 is rounded and substantially smooth along its outer surface 202 and includes a substantially square recessed section 204 along the center thereof. The cover 200 includes first and second seals 206, 208 for application against the rectangular shaped hand plates 34,35 forming the shaft of the surgical stapler 20 such that bodily tissues and other fluids do not enter the operating components of the surgical stapler 20. While specific shapes are disclosed in describing a preferred embodiment of the present invention, those skilled in the art will appreciate the shapes may be varied to suit specific surgical staplers, or other surgical instruments.

In accordance with a preferred embodiment of the present invention, the cover 200 is composed of a first cover member 210 and a second cover member 212 which can be made from various biocompatible materials, such as extruded or injection molded plastics and/or metals. The first and second cover members 210, 212 are shaped and dimensioned for selective frictional engagement via a snap connection. In this way, the cover 200 may be selectively snapped and secured about the surgical stapler 20 when it is desirable to utilize such a cover 200, for example, during the performance of hand assisted laparoscopic surgery.

More particular, the first cover member 210 includes an outer surface 214 and an opposed inner surface 216. As mentioned above, the outer surface 214 is a substantially smooth surface designed to minimize traumatic contact with the lap disc and/or bodily tissue as it is maneuvered within the body during laparoscopic procedures. The inner surface 216 includes a central recess 218 to accommodate the shaft of the surgical stapler 20, and is accordingly shaped and dimensioned to substantially conform to the shape of the shaft of the surgical stapler 20 over which it is desired to be positioned. The recess 218 extends from the first end 220 of the first cover member 210 to the second end 222 of the first cover member 210, with lateral walls 224, 226 of the recess 218 defining the upper and lower boundaries of the recess 218.

Similarly, the second cover member 212 includes an outer surface 228 and an opposed inner surface 230. The outer surface 228 is a substantially smooth surface designed to minimize traumatic contact with the lap disc and/or bodily tissue as it is maneuvered within the body during laparoscopic procedures. The inner surface 230 includes a central recess 232 to accommodate the shaft of the surgical stapler 20, and is accordingly shaped and dimensioned to substantially conform to the shape of the shaft of the surgical stapler 20 over which it is desired to be positioned. The recess 232 extends from the first end 234 of the second cover member 212 to the second end 236 of the second cover member 212, with lateral walls 238, 240 of the recess 232 defining the upper and lower boundaries of the recess 232.

The lateral walls 224, 226 of the first cover member 210 are provided with coupling members 242 shaped and dimensioned for selective engagement with mating coupling members 244 formed along the lateral walls 238, 240 of the second cover member 212. In accordance with a preferred embodiment of the present invention, the coupling members 242, 244 are snap connectors shaped and dimensioned for selective frictional engagement. Although not shown in detail, those skilled in the art will appreciate, the snap connector coupling members 242, 244 are respectively male and female parts that interfit in a frictionally engaging manner to holding the first and second cover members 210, 212 together. However, those skilled in the art will further appreciate that a variety of coupling structures may be utilized without departing from the spirit of the present invention.

In addition to coupling of the first and second cover members 210, 212 to create a cover 200 in accordance with a preferred embodiment of the present invention, and as briefly discussed above, the cover 200 is provided with first and second seals 206, 208 to prevent the passage of tissue and bodily fluid within the space defined by the respective recesses 218, 232 of the first and second cover members 210, 212. The respective first and second seals 206, 208 are composed of seal members 246, 248 formed at the first and second ends 250, 252, 254, 256 of the cover members 210, 212. These seal members 246, 248 are aligned to define the first and second seals 206, 208 at the first and second ends 258, 260 of the cover 200 when it is fully assembled.

By providing the cover 200 with a rounded, smooth outer surface 202, passage of the surgical stapler 20 is less likely to cause tearing or damage to the flexible seal of the lap disc while it is passed therethrough during hand assisted laparoscopic surgery. In addition, the smooth cover 20 will allow a surgeon to insuflate the abdomen for lower abdominal resection or other surgical resection.

Figures 11, 12:
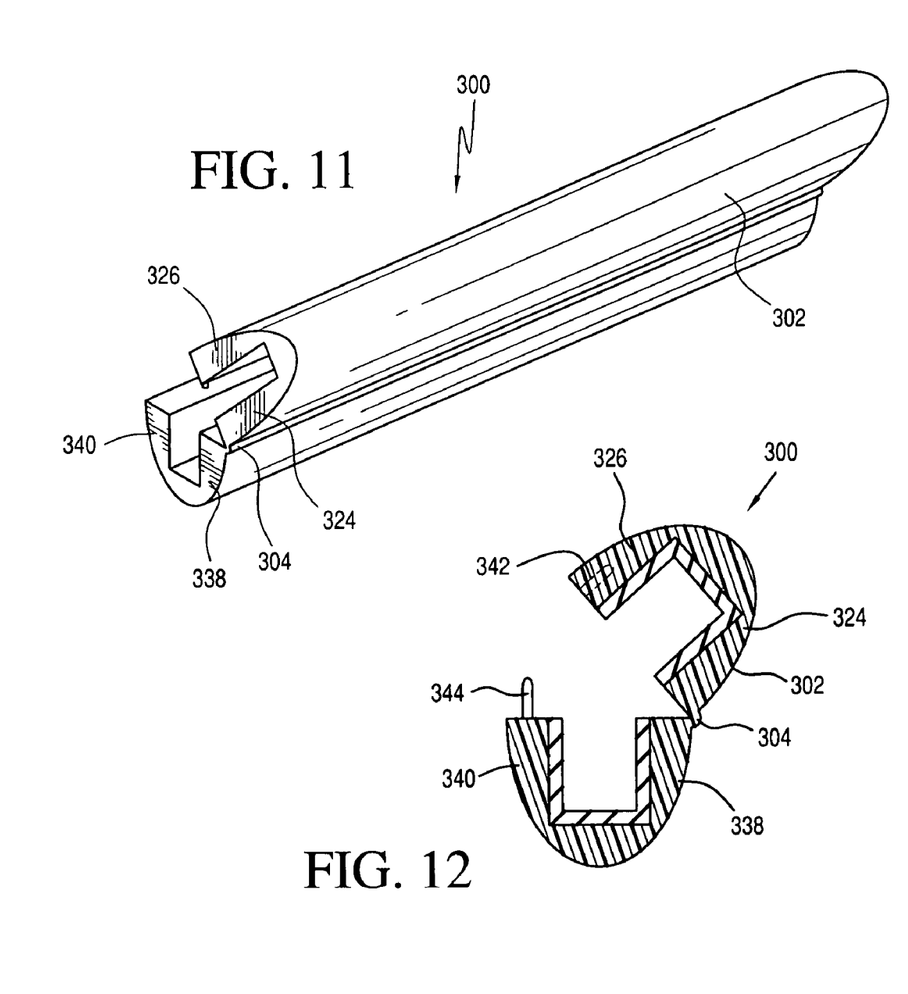
FIGS. 11 and 12 are respectively a perspective view and a cross sectional view of a cover in accordance with an alternate embodiment.

In accordance with an alternate embodiment, and with reference to FIGS. 11 and 12, the cover 300 is composed of a one piece body member 302 that is shaped and dimensioned for application about the outside of the surgical instrument via a "clam shell" design. This embodiment is substantially similar to the two-piece construction described above, but includes a living hinge 304 along one edge connecting one set of inwardly directed flange members 324, 338. This embodiment also includes mating coupling members 342, 344 respectively along the other lateral walls 326, 340 for selective coupling.

The present linear surgical stapler is constructed in a manner similar to commonly owned and copending applications. As such, further details regarding the structure and operation of the linear surgical stapler 20 may be found in commonly owned U.S. patent application Ser. No. 11/014,906, filed Dec. 20, 2004, entitled "CLOSURE PLATE LOCKOUT FOR A CURVED CUTTER STAPLER", which is incorporated herein by reference.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A surgical stapler, comprising:
a handle at a first proximal end and an end effector at an opposite distal end, at least one structural plate connecting the handle to the end effector, the handle including a firing trigger for actuating a cartridge housing and anvil positioned at the end effector with operating components of the surgical stapler extending between the handle and the end effector; and
a cover positioned about the structural plate, the cover including a cover body shaped and dimensioned for fitting about the structural plate;
the cover includes an outer surface and a central recessed section shaped and dimensioned for housing the structural plate in a manner fully covering the structural plate to prevent bodily tissues and other fluids from entering the operating components of the surgical stapler; and
further including at least one seal formed along the recessed section for engaging the structural plate.

2. The surgical stapler according to claim 1, wherein the cover body includes a substantially smooth outer surface.

3. The surgical stapler according to claim 1, wherein the first cover member and the second cover member are connected by a living hinge.

4. The surgical stapler according to claim 1, wherein the first cover member and second cover member are selectively connected via a snap connection.

5. The surgical stapler according to claim 1, wherein the first cover member includes an outer surface and an opposed inner surface including a central recess and the second cover member includes an outer surface and an opposed inner surface including a central recess.

6. The surgical stapler according to claim 1, wherein the cover includes a first end and a second end, and a first seal is positioned adjacent the first end of the cover and a second seal is positioned adjacent the second end of the cover.

7. The surgical stapler according to claim 1, wherein the cover body includes a substantially smooth outer surface.

8. A cover for a surgical stapler, comprising:
a cover body shaped and dimensioned for fitting about a shaft of a surgical stapler, the cover body including a substantially smooth outer surface and a recessed section shaped and dimensioned for positioning about a surgical stapler;
the cover body includes a first cover member and a second cover member, the first cover member and the second cover member are shaped and dimensioned for selective frictional engagement in a manner allowing for attachment to the surgical stapler;
the first cover member includes an outer surface and an opposed inner surface, the outer surface is shaped and dimensioned to minimize traumatic contact and the inner surface includes a central recess shaped and dimensioned to accommodate the shaft of the surgical stapler, the recess extends from a first end of the first cover member to a second end of the first cover member, with lateral walls of the central recess defining upper and lower boundaries of the central recess;
the cover body further includes a first seal and second seal to prevent the passage of tissue and bodily fluid within the space defined by the recessed section, the respective first seal and second seal formed at a first end and a second ends of the cover;
the second cover member includes an outer surface and an opposed inner surface, the outer surface is shaped and dimensioned to minimize traumatic contact and the inner surface includes a central recess shaped and dimensioned to accommodate a shaft of the surgical stapler, the recess extends from a first end of the second cover member to a second end of the second cover member, with lateral walls of the central recess defining upper and lower boundaries of the central recess; and
wherein the first seal and the second seal are composed of seal members formed at the first end and the second end of the respective first cover member and the second cover, these seal members are aligned to define the first seal and the second seal at the first end and the second end of the cover when it is fully assembled.

9. The cover according to claim 8, wherein the first cover member and the second cover member are connected by a living hinge.

10. The cover according to claim 8, wherein the first cover member and second cover member are selectively connected via a snap connection.

* * * * *